United States Patent [19]

Klink et al.

[11] Patent Number: 5,574,020
[45] Date of Patent: Nov. 12, 1996

[54] TILMICOSIN FORMULATION

[75] Inventors: Paul R. Klink; Thomas D. Thomson, both of Greenfield, Ind.

[73] Assignee: Eli Lilly and Company, Indianapolis, Ind.

[21] Appl. No.: 372,697

[22] Filed: Jan. 13, 1995

Related U.S. Application Data

[63] Continuation of Ser. No. 747,221, Aug. 19, 1991, abandoned, which is a continuation of Ser. No. 414,037, Sep. 28, 1989, abandoned.

[51] Int. Cl.⁶ .................................................. A61K 31/70
[52] U.S. Cl. .............................................. 514/30; 536/7.1
[58] Field of Search ................................ 514/30; 424/78; 536/7.1

[56] References Cited

U.S. PATENT DOCUMENTS 4,820,695  4/1989  Debono et al. ........................ 514/536

OTHER PUBLICATIONS

E. E. Ose et al., "Single–dose Treatment of Neonatal Calf Pneumonia with the new Macrolide Antibiotic Tilmicosin", *Veterinary Record* (1988) 123, 367–369.

*Primary Examiner*—Elli Peselev
*Attorney, Agent, or Firm*—Paul R. Cantrell; Kathleen R. S. Page

[57]    ABSTRACT

An aqueous, injectable, sustained release tilmicosin formulation comprises 250-350 mg/ml of tilmicosin and 250 mg/ml of propylene glycol, and has a pH adjusted to 6.

3 Claims, No Drawings

TILMICOSIN FORMULATION

This application is a continuation of application Ser. No. 07/747,221, filed on Aug. 19, 1991, now abandoned, which is a continuation of application Ser. No. 07/414,037, filed on Sep. 28, 1989 now abandoned.

This invention provides an improved aqueous, injectable, sustained release formulation of tilmicosin.

Tilmicosin is a macrolide antibiotic, 20-dihydro-20-deoxy-20-(cis-3,5-dimethylpiperidin-1-yl)-desmycosin, disclosed in U.S. Pat. No. 4,820,695. Also disclosed in U.S. Pat. No. 4,820,695 is an injectable, aqueous formulation comprising 50% (by volume) propylene glycol, 4% (by volume) benzyl alcohol, and 50 to 500 mg/ml of active ingredient.

Tilmicosin has been found to be useful in treatment of respiratory infections, particularly *Pasteurella haemolytica* infections in cattle when administered by injection. Accordingly, tilmicosin may be used in treatment of, for example, neonatal calf pneumonia and bovine respiratory disease complex (shipping fever).

The ideal formulation for tilmicosin in this application would be one that enables a single injection to provide therapeutic levels of tilmicosin in lung tissue over a four day (96 hour) period. At the same time, it is important that peak serum and tissue concentrations not reach toxic levels. A serum level above about 5.0 µg/ml should be avoided. Another important consideration is that at the end of the four day treatment period it is desirable to have minimal residues of tilmicosin at the injection site.

The 50% propylene glycol formulation disclosed in U.S. Pat. No. 4,820,695 releases tilmicosin from the injection site very slowly. One result is that a large dose is required to produce therapeutic levels. Because one injection site may not be adequate to accommodate one large injection, more than a single injection may be necessary. Another result is that large residues remain at the end of the four day treatment period.

The present invention provides an aqueous, injectable, sustained release tilmicosin formulation comprising:

tilmicosin 250–350 mg/ml and propylene glycol 250 mg/ml, and having a pH adjusted to 6.

The preferred concentration of tilmicosin is 300 mg/ml.

In a preferred example, the pH of the formulation is adjusted to 6 by addition of phosphoric acid.

The formulation may be prepared by slurrying the tilmicosin in water, adding phosphoric acid to provide pH 6, and adding the propylene glycol.

It will be understood that some variation in the concentration of tilmicosin, the concentration of propylene glycol, and the pH is possible without departing from the spirit of the invention. In regard to concentration of tilmicosin, it is desirable to use as high a concentration as possible so that the volume of the injection may be minimized. However, concentrations above about 300 mg/ml produce solutions that are highly viscous and may be difficult to administer, particularly in cold weather.

Acids other than phosphoric acid can be used to adjust the pH. Appropriate acids include organic and inorganic acids such as, for example, sulfuric, hydrochloric, acetic, succinic, citric, lactic, maleic, fumaric, palmitic, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic, and like acids.

A low pH of the formulation tends to increase the rate at which tilmicosin is released from the injection site. Conversely, a high pH retards release of tilmicosin. Both increasing and decreasing the propylene glycol concentration of the formulation from the 25% level have been found to reduce the area under the serum level versus time curve during the four day treatment period. Accordingly, any substantial departure from the 25% level should usually be accompanied by a downward adjustment of the pH. At a pH of 4, acceptable release characteristics have been obtained with a propylene glycol concentration as high as 414 mg/ml. Acceptable release characteristics have also been obtained with a propylene glycol concentration of 200 mg/ml at a pH of 6.

In using the formulation, cattle are typically injected with sufficient formulation to provide from 5 to 30 mg/kg of tilmicosin. The injection is typically administered subcutaneously in the neck.

TEST DATA

In a series of experiments, the serum tilmicosin level was measured over 96 hours in cattle that received a single 30 mg/kg injection. Various aqueous formulations were tested. Each formulation was administered to six animals, and peak serum concentration as well as area under the serum level vs time curve are reported in the following Table I. It is desirable to maximize the area under the serum level vs curve, provided that the peak serum level does not approach toxic levels.

TABLE I

| Formulation composition | | | Release characteristics | |
|---|---|---|---|---|
| Tilmicosin (mg/ml) | Propylene glycol (mg/ml) | pH | Peak serum concentration (µg/ml) | Area under curve 0–96 hr (µg hr/ml) |
| 300 | 414 | 8 | 0.8 | 43 |
| 300 | 400 | 6 | 1.9 | 66 |
| 300 | 414 | 4 | 2.8 | 89 |
| 300 | 300 | 6 | 1.9 | 56 |
| 300 | 250 | 6.5 | 2.1 | 62 |
| 300 | 250 | 6 | 3.4 | 115 |
| 300 | 250 | 6 | 2.4 | 99 |
| 300 | 207 | 8 | 2.0 | 77 |
| 300 | 207 | 8 | 2.0 | 65 |
| 300 | 200 | 6 | 3.0 | 85 |
| 300 | 207 | 4 | 3.9 | 90 |

It will be observed from the data in Table I that superior release characteristics are exhibited by the aqueous tilmicosin formulation containing 250 mg/ml of propylene glycol and having a pH of 6, and that the formulation containing substantially more propylene glycol and having a pH of 8, which approximates the formulation disclosed in U.S. Pat. No. 4,820,695, exhibited unsatisfactorily slow release characteristics.

We claim:

1. An aqueous injectable tilmicosin formulation comprising:

tilmicosin 250–350 mg/ml and propylene glycol 250 mg/ml, and having a pH adjusted to 6.

2. The formulation of claim 1 comprising 300 mg/ml of tilmicosin.

3. The formulation of claim 2 wherein phosphoric acid is used to adjust the pH.

* * * * *